US011653896B2

United States Patent
Lindenroth et al.

(10) Patent No.: US 11,653,896 B2
(45) Date of Patent: May 23, 2023

(54) ACTIVE STEERING FOR INTRACARDIAC ECHOCARDIOGRAPHY CATHETERS

(71) Applicant: Siemens Healthcare GmbH, Erlangen (DE)

(72) Inventors: Lukas Lindenroth, London (GB); Erin Girard, Madison, CT (US); Rodolfo Finocchi, Cambridge, MA (US); Young-Ho Kim, West Windsor, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 689 days.

(21) Appl. No.: 16/544,091

(22) Filed: Aug. 19, 2019

(65) Prior Publication Data

US 2020/0060646 A1 Feb. 27, 2020

Related U.S. Application Data

(60) Provisional application No. 62/720,539, filed on Aug. 21, 2018.

(51) Int. Cl.
*A61B 8/12* (2006.01)
*A61B 8/00* (2006.01)
*A61M 25/01* (2006.01)

(52) U.S. Cl.
CPC .............. *A61B 8/12* (2013.01); *A61B 8/42* (2013.01); *A61B 8/445* (2013.01); *A61B 8/4488* (2013.01); *A61M 25/0113* (2013.01); *A61M 25/0136* (2013.01); *A61M 25/0147* (2013.01)

(58) Field of Classification Search
CPC ........... A61B 8/12; A61B 8/4483; A61B 8/42; A61B 8/445; A61B 8/4488; A61B 8/0883; A61B 8/4461; A61M 25/0113; A61M 25/0136; A61M 25/0147
See application file for complete search history.

(56) References Cited

U.S. PATENT DOCUMENTS 4,951,677 A * 8/1990 Crowley ................. A61B 8/12
600/463
5,462,527 A * 10/1995 Stevens-Wright .........................
A61M 25/0147
604/95.04

(Continued)

OTHER PUBLICATIONS

Corindus "Corpath GRX Precision Vascular Robotics" retrieved at https://www.corindus.com/corpath-grx/now-it-works accessed Aug. 14, 2019. pp. 1-5.

(Continued)

*Primary Examiner* — Patricia J Park
*Assistant Examiner* — Adil Partap S Virk (57) ABSTRACT

For active control of steering, one or more motors integrated into an intra-cardiac echocardiography catheter handle control the bending. Multiple sets of motors may be used to control steering wires anchored at different segments along the catheter, allowing steering with multiple bends in complex patterns controlled by a controller. The handle may be releasably separated into a reusable motor part and a disposable steering wire part so that the more complex and expensive motor part is not discarded and so that the number of motors may be matched to the number of steering wires.

15 Claims, 4 Drawing Sheets

(56) References Cited

U.S. PATENT DOCUMENTS

| | | | | |
|---|---|---|---|---|
| 5,549,542 | A * | 8/1996 | Kovalcheck | A61B 1/0052 600/150 |
| 2003/0109778 | A1* | 6/2003 | Rashidi | A61B 18/1492 606/41 |
| 2004/0176757 | A1* | 9/2004 | Sinelnikov | A61B 17/2202 606/27 |
| 2005/0228290 | A1* | 10/2005 | Borovsky | A61B 8/12 600/467 |
| 2007/0073389 | A1* | 3/2007 | Bolduc | A61F 2/07 623/1.36 |
| 2007/0167813 | A1* | 7/2007 | Lee | A61B 8/4488 600/459 |
| 2008/0009745 | A1* | 1/2008 | Hossack | A61B 8/483 600/463 |
| 2008/0312536 | A1* | 12/2008 | Dala-Krishna | A61B 8/445 600/459 |
| 2010/0179426 | A1* | 7/2010 | Davies | A61B 8/4483 600/439 |
| 2011/0144576 | A1 | 6/2011 | Rothe | |
| 2011/0263983 | A1* | 10/2011 | Peszynski | A61B 8/445 600/443 |
| 2013/0046318 | A1* | 2/2013 | Radgowski | A61B 34/30 606/130 |
| 2013/0102960 | A1* | 4/2013 | Miyoshi | A61M 25/0136 604/95.04 |
| 2014/0046313 | A1* | 2/2014 | Pederson | A61B 17/2202 606/28 |
| 2016/0206853 | A1* | 7/2016 | Bolduc | A61M 25/0133 |
| 2016/0287840 | A1* | 10/2016 | Jiang | A61M 25/0147 |
| 2017/0000648 | A1* | 1/2017 | Chabrier | A61F 9/00821 600/467 |
| 2018/0071487 | A1* | 3/2018 | Khuu | A61M 25/0147 |
| 2019/0142537 | A1* | 5/2019 | Covington | A61B 34/30 606/108 |

OTHER PUBLICATIONS

Dicardiology "FDA Clears Hansen Magellan Robotic System for Peripheral Vascular Interventions" retrieved at https://www.dicardiology.com/product/fda-clears-hansen-magellan-robotic-system-peripheral-vascular-interventionsDated Jun. 5, 2012. pp. 1-3.

Loschak, Paul M., et al. "A 4-DOF robot for positioning ultrasound imaging catheters." ASME 2015 International Design Engineering Technical Conferences and Computers and Information in Engineering Conference. American Society of Mechanical Engineers, 2015. pp. 1-10.

Medgadget "Sensei X Robotic Catheter System for Electrophysiology Procedures" retrieved at https://www.medgadget.com/2009/09/sensei_x_robotic_catheter_system_for_electrophysiology_procedures.html Dated Sep. 18, 2009. pp. 1-4.

* cited by examiner

ACTIVE STEERING FOR INTRACARDIAC ECHOCARDIOGRAPHY CATHETERS

RELATED APPLICATION

The present patent document claims the benefit of the filing date under 35 U.S.C. § 119(e) of Provisional U.S. Patent Application Ser. No. 62/720,539, filed Aug. 21, 2018, which is hereby incorporated by reference.

BACKGROUND

The present embodiments relate to steering intracardiac echocardiography catheters (ICE). Cardiac catheters are commonly steered in 4 degrees of freedom. The catheter may be bent along two principal axes of the catheter by turning two independent knobs placed on the catheter's handle. The knobs are often labelled "anterior-posterior" for one bending plane and "left-right" for the perpendicular bending plane, both with respect to the catheter reference frame. This steering provides for one bend in the catheter. In addition to the bending, the clinician may translate and rotate the catheter tip along and around its longitudinal axis by translating and rotating the catheter handle, respectively.

Difficult catheter manipulability is a major challenge for the operating surgeon. As part of, for example, electrophysiological interventions, the ICE catheter has to be moved in a coordinated fashion with an interventional catheter to not lose view on the latter. This can pose a significant challenge to the operator, who has to manipulate multiple but limited degrees of freedom simultaneously to achieve a desired pose of the ICE catheter. The limited ability to control bending is difficult in procedures such as mitral valve replacement, which may benefit from more complex catheter motions and bending than achievable with current systems.

SUMMARY

By way of introduction, the preferred embodiments described below include methods, systems, and catheters for active control of steering. One or more motors integrated into the catheter handle control the bending. Multiple sets of motors may be used to control steering wires anchored at different segments along the catheter, allowing steering with multiple bends in complex patterns controlled by a controller. The handle may be releasably separated into a reusable motor part and a disposable steering wire part so that the more complex and expensive motor part is not discarded and so that the number of motors may be matched to the number of steering wires.

In a first aspect, a medical ultrasound system is provided for intra-cardiac echocardiography. An intra-cardiac echocardiography catheter has a tip, a handle, steering wires, and an ultrasound transducer array. A plurality of motors connects without gearing to the steering wires of the intra-cardiac echocardiography catheter. The motors are in the handle of the intra-cardiac echocardiography catheter.

In one embodiment, the ultrasound transducer array is a one-dimensional array of transducer elements for scanning a patient within the field of view. The one-dimensional array is on a distal end of the intra-cardiac echocardiography catheter for insertion within the patient.

The steering wires control a bend at a distal end of the intra-cardiac echocardiography catheter. In a further embodiment, two groups of at least three steering wires per group connect to different segments at different positions along the intra-cardiac echocardiography catheter. The steering wires of one of the two groups connect to a first rigid plate in one of the different segments, and the steering wires of another of the two groups connect to a second rigid plate in another of the different segments.

The motors may be linear motors or other actuators. In one embodiment, shafts of the motors directly connect to the steering wires.

In an embodiment, the handle has a steering wire housing part connected to the intra-cardiac echocardiography catheter and a motor housing part connected to a power cable and housing the motors. The steering wire housing part is releasable from the motor housing part. For example, the shafts of the motors have shaped ends releasably mateable with holders connected to the steering wires. The steering wire housing part is connectable with the motor housing part by rotation to mate the shaped ends with the holders. In a further embodiment, the motor housing part is configured for operation with different ones of the steering wire housing parts. The steering wire housing parts and connected intra-cardiac echocardiography catheters are disposable, and the motor housing part is reusable.

In another embodiment, a rotation sensor is in the handle. A controller is configured to maintain a position of the tip relative to a patient during rotation of the handle by actuation of one or more of the motors in response to sensed rotation from the rotation sensor.

In yet other embodiments, a controller is configured to control the motors based on landmarks detected using scanning from the ultrasound transducer array. One or more input sensors on the handle are configured for steering the intra-cardiac echocardiography catheter from user input based on control of the motors.

In a second aspect, a method is provided for controlled bending in a catheter. A linear motor in a handle of an intra-cardiac echocardiography catheter is controlled. The intra-cardiac echocardiography catheter is steered by the motor control through a steering wire connected with a shaft of the linear motor.

In one embodiment, six or more of the linear motors connected with six or more of the steering wires are controlled. Different ones of the steering wires connect to different segments of the intra-cardiac echocardiography catheter. Bending for one of the different segments is different than for another of the different segments by the motor control of the six or more linear motors.

In another embodiment, one part of the handle having the motor is releasably connectable to another part of the handle having a terminal end of the steering wire. The connecting mates a shaft of the linear motor to the steering wire.

A patient may be imaged with ultrasound scanning from the intra-cardiac echocardiography catheter as steered.

In a third aspect, a medical ultrasound system is provided for intra-cardiac echocardiography. An intra-cardiac echocardiography catheter has a tip, a handle, steering wires, and an ultrasound transducer array. A plurality of linear motors connects to the steering wires of the intra-cardiac echocardiography catheter. The motors are in the handle of the intra-cardiac echocardiography catheter.

In a further embodiment, the linear motors and steering wires are arranged in two or more groups connected to steer two or more segments of the intra-cardiac echocardiography catheter. In another embodiment, the handle has a first part releasably connectable to a second part. The first part houses the linear motors, and the second part has a termination end of the steering wires.

The present invention is defined by the following claims, and nothing in this section should be taken as a limitation on those claims. Features of one aspect or type of claim (e.g., method or system) may be used in other aspects or types of claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

For steering, the handle of an ICE catheter includes integrated actuators. For example, active steering is achieved by integrating linear motors in the catheter handle. The motors actuate catheter movement by applying pushing or pulling forces on the catheter tendons or steering wires individually to bend the catheter tip and/or other segments. The operator is therefore only required to provide an input bending angle for the distal end of the catheter, which is then accomplished by the actuators. Actuating parts of the catheter motion may improve the role of ICE in clinical interventions and improve the overall practicality of usage by reducing the catheter control complexity for the operator.

A ICE catheter body may be modified to include multiple segments that are separately steered. A greater catheter dexterity is achieved by adding a multitude of bending segments to the catheter tip which would be difficult to control manually. Using motors to control different segments avoids the complication of manual steering each segment separately.

Connecting motors to the steering wires without transmission reduces slack, which is commonly present in commercially available catheter systems and greatly worsens the controllability of the system. Slack is compensated by directly applying tension to the catheter tendons.

Use of the motors to steer may reduce stress for the operator caused by continuous manual steering of the catheter tip and at the same time improve the functionality of the system. The system combines an active steering mechanism with a handle design to allow for assistive control of the catheter bending while giving the operator the ability to manually manipulate the catheter handle. This improves ergonomic factors for the operating clinician and allows for more degrees of freedom to be integrated in the catheter.

Another advantage is provided by separating the handle into parts. A catheter and pulley element are disposable, and the motor and cable elements are reusable, allowing for easy sterilization of the system in a clinical setting.

Figure 1:
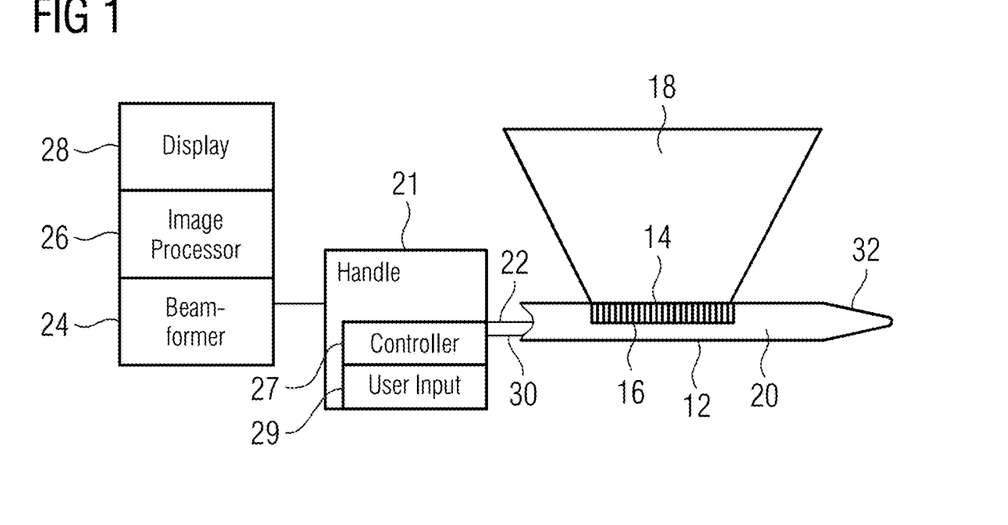
FIG. 1 is a block diagram of one embodiment of a medical ultrasound system for active steering with motors.

FIG. 1 shows a medical ultrasound system for ICE. The system with the corresponding catheter uses integrated motors for active steering. The motors are positioned in the handle of the ICE catheter for pushing and pulling on steering wires. Due to active control, multiple segments may be provided for more complex steering.

The medical ultrasound system includes the intra-cardiac echocardiography catheter 12, a beamformer 24, an image processor 26, and a display 28. Additional, different, or fewer components may be provided. For example, the system includes the array 14 in a catheter 12 without the beamformer 24, image processor 26, and/or display 28. These imaging electronics may be in a separate ultrasound imaging system. The catheter 12 releasably connects with the imaging system. As another example, the system is for ablation or other purpose than ultrasound. An ablation or other type of catheter is used without the beamformer 24, image processor 26, and/or display 28.

The intra-cardiac echocardiography catheter 12 includes an array 14 of elements 16 for imaging within a shaft or housing 20 having a tip 32, electrical conductors 22, steering wires 30, and a handle 21. Additional, different, or fewer components may be provided, such as radio opaque markers, ablation electrodes, lens, needle guide, or ports.

The housing 20 is PEBAX, nylon, polymer, or other flexible material. The housing 20 is formed around the array 14 and other parts extending from the handle 21 and insertable into the patient. In other embodiments, the housing 20 includes one or more windows or openings through which the array 14 is exposed. The housing 20 is configured for insertion into a circulatory system of a patient. For example, the distal tip 32 of the catheter 12 includes a more flexible portion covered by the housing 20 for moving through the circulatory system. Steering wires 30 connected to the housing 20 or parts (e.g., anchors) within the housing 20 are configured to guide the housing 20 within the circulatory system.

The array 14 has a plurality of elements 16, backing block, electrodes, and a matching layer. Additional, different, or fewer components may be provided. For example, two, three, or more matching layers are used. The backing block material absorbs and/or reflects acoustic energy. The matching layers provide a more gradual transition between acoustic impedance, minimizing reflection from the boundary between the transducer and the patient. The electrodes interact with the elements to transduce between acoustic and electrical energy. The variation of potential or distance between electrodes across an element 16 causes electrical signal or acoustic energy generation, respectively. In one embodiment, a flex circuit connect from the elements 16 to a bundle of conductors 22 that carry the signals between the beamformer 24 and the array 14.

Any number of elements 16 may be provided, such as 64 elements. 128 or other number of elements 16 may allow for larger apertures and/or a greater number of apertures. The elements 16 are adjacent to each other, such as having substantially wavelength or less spacing between the centers of adjacent elements 16. For example, the elements 16 have half wavelength spacing with kerfs acoustically separating each element 24. Sparse arrays 12 with greater spacing between elements 16 may be used.

The elements 16 are positioned along an azimuth axis of the array 14 (longitudinal axis of the catheter 12). For a one-dimensional array 14, the elements 16 are in a single row along the azimuth axis. The array 14 may be linear or curved linear. For use in a catheter, the azimuth axis is along the longitudinal axis of the catheter 12 but may be offset from the axis or centered along the axis. The array 14 of the elements 16 is of any length, such as 7 mm, 14 mm, or 28 mm. Multi-dimensional arrays 14 may be used, such as 1.25, 1.5, 1.75 or 2D arrays. In one embodiment for volume imaging from a thin and long catheter, the array 14 twists about the longitudinal or azimuth axis of the array or an axis spaced from the center of the array. Different elements 16 or groups of elements 16 face in different directions. For example, the twist follows a helical pattern. By walking an aperture along the array 14, different scan planes spaced or fanned apart in elevation are defined and used for scanning. This allows scanning of a volume with the linear array.

The array 14 is positioned within the catheter 12. The array 14 may fit within 10 French, 3.33 mm, 12.5 French, or another diameter catheter 12. The array 14 is at a distal end or tip 32 of the catheter 12, such as being within 20 mm of an end of the tip 32 or a beginning of a flexible tip portion. The array 14 may have any position within the catheter 12 that results in the array 14 being within the patient during use of the catheter 12 for imaging.

The transducer array 14 is used for ultrasound imaging. The images assist in diagnosis, catheter guidance, needle guidance, ablation guidance, placement, and/or needle puncture. The side of the elements 16 covered by the matching layer, closer to the region to be scanned and/or opposite the backing block, is the emitting face of the array 14. Acoustic energy is transmitted from and received at the emitting face of the array 14. The angle of acoustic energy relative to the emitting face affects the sensitivity of the elements 16 to the energy. The elements 16 are more sensitive to the energy at normal incidence to the elements 16. The array 14 scans in a field of view 18 in a plane perpendicular to the emitting face. The array 14 is used to scan in the field of view 18 or region of desired sensitivity to any desired depth. This field of view 18 of the array 14 has any format for the corresponding scan pattern, such as Vector®, sector, or linear. The patient within the field of view 18 may be imaged using the array 14.

Electrical conductors 22 connect the elements 16 of the array 14 to the beamformer 24. The conductors 22 are cables, coaxial cables, traces on flexible circuit material, wires, continuation of the flex circuits, wire jumpers, combinations thereof, and/or other now known or later developed conductor. One conductor 22 is provided for each element 16. Alternatively, fewer conductors 22 than elements 16 may be used, such as for switched apertures, partial beamforming, or multiplexing. The conductors 22 are separately addressable by the beamformer 24. Each element 16 may be selectively used for a given aperture and associated electronic steering. Alternatively, some elements 16 are useable with only a subset of possible apertures.

Figure 5:
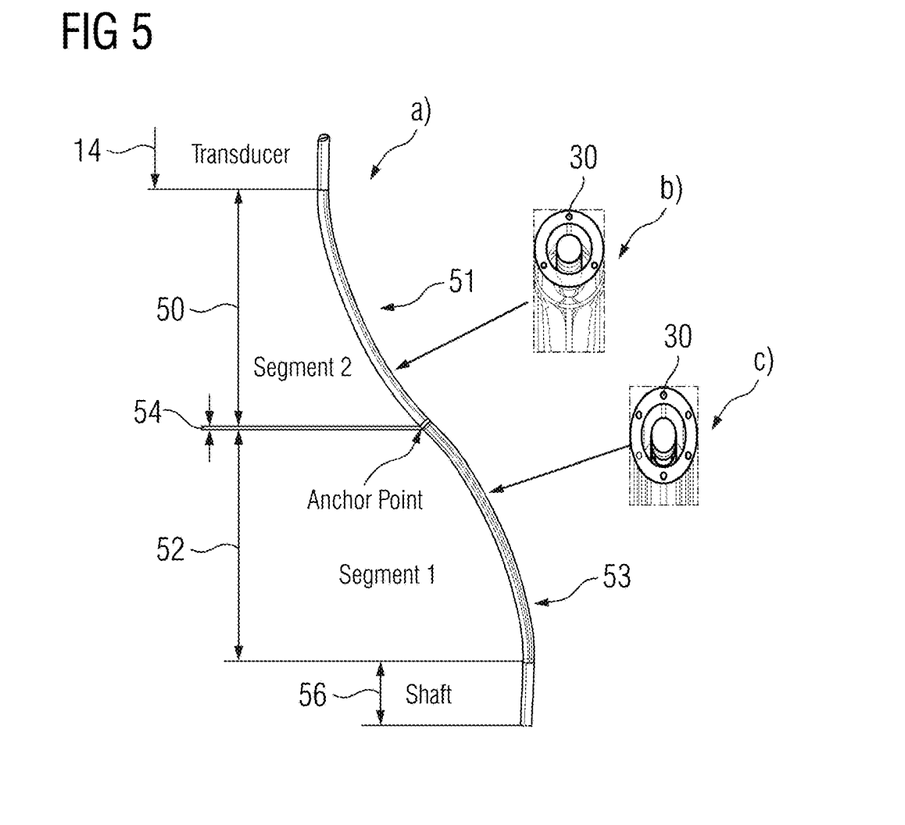
FIG. 5 illustrates bending in different segments along an ICE catheter.

The steering wires 30 are cables, tendons, or other structure for transferring push and pull force from the handle 21 to a portion of the catheter 12 within a patient, such as to the distal end or the tip 32. Any material may be used, such as plastic, fiberglass, or metal. Any number of steering wires 30 may be used, such as three or four wires. For example, three steering wires 30 offset from the center in an equal spacing about the center or longitudinal axis may be used to steer along two perpendicular planes. The steering wires 30 run through the elastic material of the catheter body or housing 20 to the distal end and are arranged in a circular fashion around a central channel, which provides sufficient space for the ultrasound transducer cable or conductors 22 to be guided through. The relative force between the steering wires 30 causes the catheter 12 to bend. For example, FIG. 5 shows the steering wires 30 causing a slight bend 51. Other degrees of bending may be provided. Any now known or later developed arrangement of steering wires 30 may be used.

The steering wires 30 control the bend 51 at a distal end of the catheter 12. The bend 51 may be at a portion of the catheter 12 adjacent to the distal end or tip 20, such as providing for the array 14 to be spaced from the handle 25 by the bend 51. For example, the steering wires 30 are anchored to the housing 20, transducer array 14, or a rigid insert or anchor near the distal end to cause the bend 51. The elastic body or housing 20 may be bent along its principal axes by applying tension to the attached steering wires 30. Using motors 25 instead of user-based rotation of two knobs for two planes allows for only three steering wires 30 for forming the bend 51. Four steering wires 30 with motor 25-based control may be used.

In an embodiment shown in FIG. 5, additional motors 25 and steering wires 30 are provided to form more than one bend 51, 53 at a same time. More complex shapes or bending combinations may be actively formed or steered. Different groups of steering wires 30 (e.g., at least three steering wires 30 per group) and motors 25 connect to different segments 50, 52 along the longitudinal extent of the catheter. The anchor point 54, such as part of the housing 20, a rigid insert or plate, or another anchor device or material is provided for each segment. The steering wires 30 for that group or anchor point 54 terminate at the anchor point 54. The placement of the anchor point 54 establishes the location of the bending. In the example of FIG. 5, two groups, one anchored at the anchor point 54 and the other anchored at the distal end or by the transducer array 14, may be used to form two bends 51, 53 at different locations at a same time. Each segment 50, 52 is independently steered by the corresponding group of steering wires 30.

The distal end and/or other parts along the catheter may have a number N of steerable segments 50, 52. This allows for greater maneuverability of the catheter tip 32 and can be beneficial to clinical procedures such as mitral valve replacement in which complex catheter motions and configurations (shapes) are desired. The catheter segments 50, 52 are separated by rigid plates that serve as anchor points 54 for the steering wires 30 actuating the corresponding segment 50, 52. A catheter with N steerable segments 50, 52 holds a minimum of N*3 steering wires 30 for actuating the individual segments 50, 52. The steering wires 30 may be distributed evenly around the circumference of the catheter body in cross section, but other arrangements may be used. In the example of FIG. 5, N is 2, so there are 6 steering wires 30. The cross-section of FIG. 5(*c*) shows six steering wires 30 distributed evenly about the center of the longitudinal axis in the bend 53 of the segment 52. Since three of the steering wires 30 terminate at the anchor point 54 for controlling the bend 53, the cross-section of FIG. 5(*b*) shows the remaining three steering wires 30 in the segment 50 for controlling the bend 51.

In a further embodiment, the amount and/or direction of bending is measured. The position of the motors 25 may be used to determine the amount and direction. Alternatively or additionally, one or more optical fibers are provided in the catheter 12. The optical fibers extend through the housing 20 to measure the bends 51, 53. Strain gauges may be used in other embodiments. The overall shape or arrangement of bends 51, 53 is measured and used for control or feedback.

Figure 2:
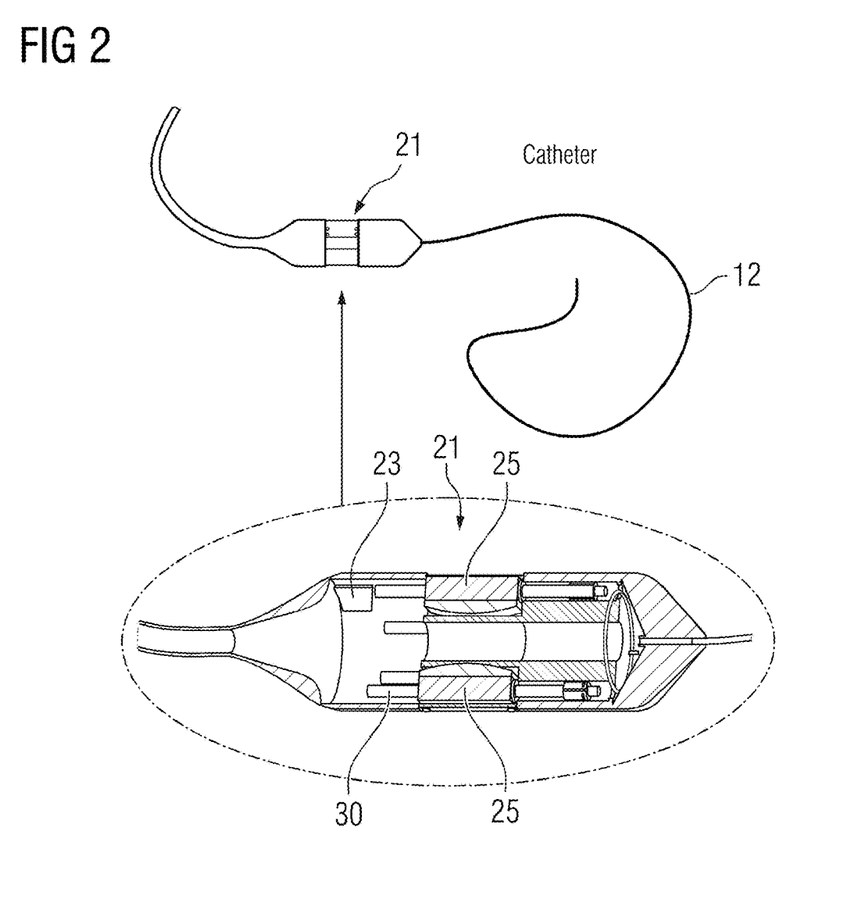
FIG. 2 illustrates one embodiment of an ICE catheter with a handle.

Referring to FIGS. 1 and 2, the handle 21 includes a housing, motors 25, a controller 27, and user input 29. Additional, different, or fewer components may be used. For example, the motors 25, controller 27, and/or user input 29 are separated from the handle 21.

The motors 25 are linear motors (e.g., linear magnetic motors), servo motors, rotational motors, or other electric, pneumatic, or hydraulic motors for applying push or pull force to the steering wires 30. A separate motor 25 is provided for each steering wire 30. Alternatively, gearing, clutch, and/or transmission is used to apply force from one motor 25 to multiple steering wires 30.

In one embodiment, the motors 25 connect to the steering wires 30 in the handle 21 without gearing, such as without a transmission. The tension from or on the steering wires 30 is the same as the tension applied to the shafts of the motors 25, so a direct connection is provided. A push rod, pulley, or other intervening device may be provided for the direct connection such that the tension is the same and/or there is no slack between motor movement and steering wire movement. The shafts directly connect to the steering wires 30. The motors 25 directly induce pulling forces in the tendons or steering wires 30 without the need for external transmissions. As tendon forces are controlled directly, slack, which is commonly present in knob-based systems, may be reduced or eliminated, and the catheter controllability therefore improved.

The motors 25 are arranged in a circular fashion around a central channel or region in the handle 21. The channel is for the conductors 22 and other communication and/or power wires. The motors 25 are equally spaced around the center but may have other spacing. The motors 25 may alternatively or additionally be stacked along the longitudinal axis using push-pull rods 38 to reduce the diameter of the handle 21 while increasing its length.

The motors 25 automate the catheter 12 bending. To actuate the bending of the catheter 12 by tendons or steering wires 30 running along the catheter 12, the motors 25 apply tendon pulling or pushing forces. This allows the operator to induce catheter 12 bending by only adjusting the user input 29 without having to apply the forces themselves.

To steer, the motors 25 apply relative push and/or pull forces on the steering wires, controlling the direction and magnitude of the bending. Any combination of relative forces may be used. Where multiple segments 50, 52 are provided, multiple bends are independently controlled, providing greater degrees of freedom. The entire handle 21 may be rotated by any amount to rotate the catheter 12 and/or array 14. A shift in a bend plane may be provided by either rotating the handle 21 or by changing the forces on the steering wires 30. By using the motors 25, the same steering may be provided as rotating the handle 25, but without rotating the handle. The bend in the catheter frame of reference is altered by the motors 25. This alteration changes the position of the catheter tip 32 and corresponding bend relative to the patient frame of reference.

The motors 25 may be used to change the bend in the catheter frame of reference to maintain the position of the bend in the patient frame of reference. The steering is used to avoid altering the bending plane. For example, the user rotates the handle 21. Instead of the rotation rotating the bends 51, 53 and the catheter tip 32, the motors 25 change the relative forces on the steering wires 30 to keep the catheter tip 32 in the same position. The planes defining the bend 40 may be maintained or fixed relative to the patient.

Referring again to FIG. 1, the user inputs 29 are devices, such as sensors, for receiving user input. For example, the user inputs 29 are electrical sensors, such as potentiometers or capacitive sensors, connected with rockers, knobs, dials, touch pads, joysticks, or other devices for steering. The user activates one or more user inputs 29 on the handle 21 for manually controlling the bend(s) 51, 53.

The user inputs 29 receive user input of steering control. The controller 27 maps those inputs into steering with respect to the catheter or patient frame of reference. Without rotation of the handle 21, an input may be received by the user inputs 29 to bend more or less in a same plane or to alter the plane in which the bend occurs relative to the catheter and/or patient frames of reference. The inputs may be for bending along two perpendicular planes, such as associated with two knobs, which inputs are then mapped to tension in the three steering wires 30 to implement the desired bend. For patient frame of reference steering, with rotation of the handle 21 and without input on the user input 29, the bend(s) 51, 53 may be maintained in a same plane(s) despite the rotation. In alternative embodiments, the rotation of the tip 32 of the catheter 12 is performed by a motor in the handle 21 without rotation of an exterior of the handle 21. The user input 29 is used to control the bending and/or rotation performed by motors 25.

In alternative embodiments, imaging or other feedback is used to control the motors 25 and corresponding bending. For example, the motors 25 are operated to maintain or place a detected landmark or device (e.g., ablation catheter) in the field of view of the array 14. In other embodiments, a pre-determined or pre-planed shape or bending arrangement is implemented. Upon activation by the user, the motors 25 are controlled to provide the shape.

In one embodiment, for manual rotation of the handle 21, a rotation sensor 23 senses the rotation of the handle 21. The rotation sensor 23 is in or on the handle 21 for sensing the rotation of the handle 21 by the user and/or to provide approximate registration of the catheter 12 with respect to the patient.

Any sensor may be used. In the embodiment shown in FIG. 2, an inertial measurement unit is provided as the rotation sensor 23 in the handle 21. In other embodiments, the user input 29 receives user input to rotate, providing sensing of the rotation. In yet other embodiments, a camera or imager with or without fiducials in or on the handle 21 is used to sense rotation. The camera or imager is spaced from the handle 21 to view the handle 21.

In one embodiment, the rotation compensation of the bend 51, 53 maintains the position of tip 32 in the patient frame of reference-based input from the sensor 23. The position may not be maintained exactly due to rotation sensor tolerance, control tolerance, patient movement, and/or translational movement. The compensation maintains by attempting to keep the bends 51, 53 in the same planes within the patient frame of reference, such as within +/−10 degrees.

During rotation of the catheter 12, the tip 32 rotates while the position is maintained. This rotation changes the field of view of the array 14, allowing imaging of other parts of the patient around the location. The user rotates the handle 21 or causes rotation of the catheter 12 to scan other planes or regions around the current location of the tip 32. The motors 25 are automatically controlled to alter the bends 51, 53 to maintain the position in the patient frame of reference while the tip 32 rotates. The orientation of the tip 32 changes while the location or position is maintained.

The handle 21 is shaped and sized for handheld guidance or use of the catheter 12. For example, the handle 21 is cylindrical with grips to be used by one hand of a surgeon. The handle 21 has a single housing made of one or more parts. The housing connects with the shaft or housing 20 of the catheter 12 and with a cable or cables for power and communications.

Figure 3:
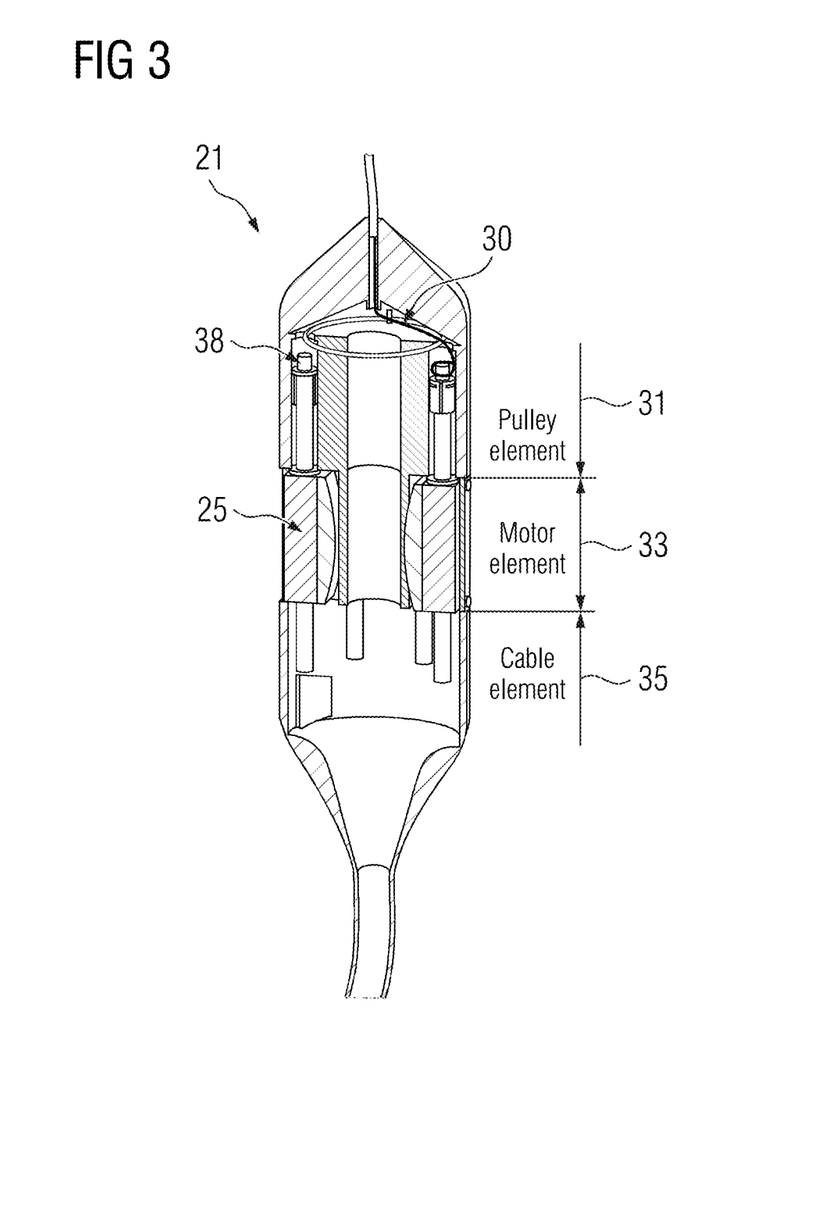
FIG. 3 illustrates an example handle for an ICE catheter.

In one embodiment, the handle 21 has multiple housings that may be releasably connected and disconnected. FIG. 3 shows an example. A cable housing 35 forms one part, a motor housing 33 forms another part, and a pulley housing 31 forms a third part. Additional or fewer parts may be provided. For example, the motor housing 33 and cable housing 35 are formed as a single part or housing for releasable connection with the housing of the pulley housing 31.

The pulley housing 31 includes terminal ends of the steering wires 30. The terminal ends extend through the pulley housing 31. Alternatively and as shown in FIG. 3, the steering wires 30 end at a pulley, such as a ring. Sliders 38, such as rods, shafts, wires, or tendons connect the pulley to an end of the pulley housing 31 opposite the shaft 20 of the catheter. Other arrangements for direct linkage may be used. In alternative embodiments, indirect linkage of the steering wires 30 to the motors 25 is provided through gears, belts, or a transmission. The pulley housing 31 diverts the catheter tendons or steering wires 30 to their respective actuators or motors 25.

The motor housing 33 includes the motors 25 and corresponding shafts for applying force to the sliders 38 or steering wires 30. The cable housing 35 includes a cable for power and/or communications. In one embodiment, the motor housing 33 and the cable housing 35 are formed as one element, which is releasably connected to the pulley housing 31. The cable housing 35 may have holes or gaps for movement of the shafts of the motors 25. Alternatively, the motor housing 33 is long enough to house the gaps or holes for shaft movement.

In another embodiment, the cable housing 35 of the handle 21 attaches to the motor housing 33 with a screw or clip connector to allow for a quick exchange of the motor housing 33 depending on the catheter configuration. The controller 27 and sensor 23 may be in the motor housing 33 and/or the cable housing 35.

The motor housing 33 is releasably connected to the pulley housing 31. Any releasable connection may be provided, such as a bolt, screw, or clip connector. In one embodiment, a tongue and groove arrangement is used for the pulley housing 31 to rotateably snap into place against the motor housing 33. A threaded, pressure, or another snap connection may be used. Rather than being formed together as an part inseparable without destruction, releasable connection through rotation, bolting, screwing, or snap fit are provided.

Figure 4:
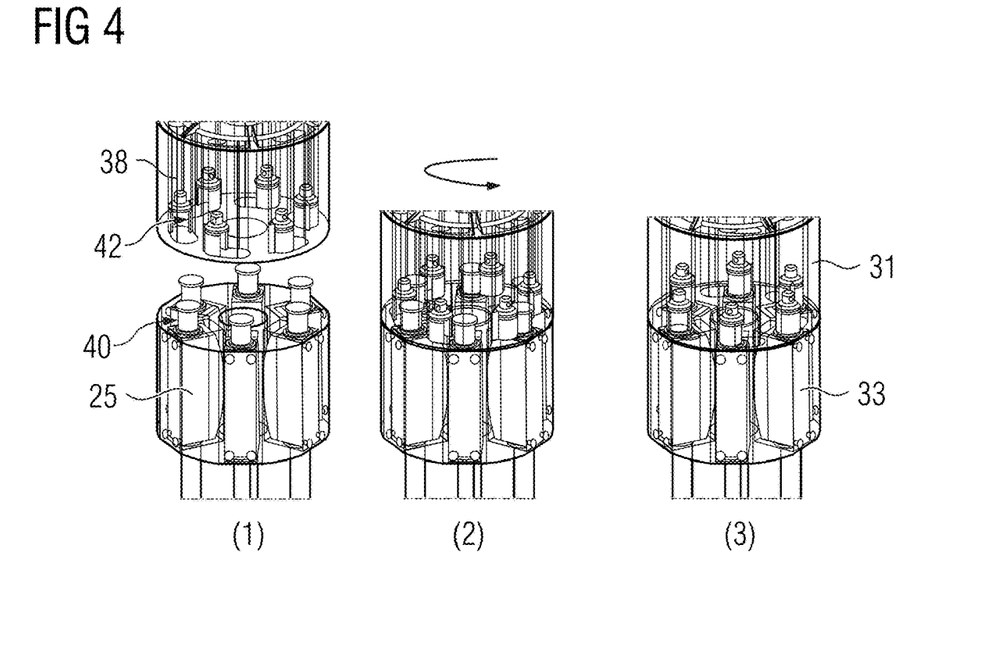
FIG. 4 illustrates releasable mating of different parts of a handle for an ICE catheter.

In one embodiment shown in FIG. 4, the shafts of the motors 25 have shaped ends 40, such as a mushroom or nail head shape. Tapered or directional shapes may be used. The shaping is for engaging with a holder 42 or receiver, such as the cups connected to the steering wires 30 through the sliders 38. A further clip-on or snap fit protrusion and receptacle structure may be formed on the housings of the pulley housing 31 and the motor housing 33. To connect, the shaped ends 40 protruding from the motor housing 33 are placed in holes adjacent to the holders 42. Other protrusions from the housings or one of the housings may extend into other holes in the housings or another one of the housings. This placement is represented in transition from FIG. 4(1) to FIG. 4(2). Once placed, the pulley housing 31 and motor housing 33 are rotated relative to each other. This rotation shifts the shaped ends 40 into the holders 42, as shown in FIG. 4(3). The pulley housing 31 is mated with and held to the motor housing 33. Similarly, the shafts of the motors 35 are directly engaged with the steering wires 30 through the holders 42 and sliders 38 for transfer of force between the steering wires 30 and the motors 25. The motor housing 33 has a number of linear motors (e.g., a minimum of N*3 linear motors where N is the number of actively bendable segments). The connection may be released by rotation and then separating the parts once disengaged by the rotation.

The power and communications may be connected and disconnected with any mating, such as spring-loaded balls, rods, or plates for contact with exposed electrodes. In one embodiment, wire clips or connectors are used.

The releasable connection may be used to maintain the motor housing 33 for use with different pulley housings 31 and corresponding catheters for insertion into the patient. Since the handle 21 is not inserted into the patient, the handle may be sterilized and kept for reuse where the pulley housing 31 and corresponding catheter 12 that was inserted into the patient may be discarded or discarded with more frequency. The catheter 12 and pulley housing 33 are disposable to maintain sterilizability of the system. The clip or releasable connection allows for disposal of the pulley housing 31 and maintaining of the more expensive motor housing 33 for repeated use.

Different numbers of segments for bending may be provided. One given motor housing 33 may be used with pulley elements 31 and corresponding catheters with different numbers of active steering segments. For example, the motor housing 33 includes six motors 25. A pulley housing 31 and corresponding catheter 12 with two bending sections includes holders 42 and sliders 38 for connecting with all six motors 25. A pulley housing 31 and corresponding catheter 12 with only one bending section includes holders 42 and sliders 38 for connecting with three of the six motors. Holes or gaps are provided for the unused motors. The same motor housing 33 may be releasably connected to different catheters 12 to form the handle.

In another embodiment, the catheter handle 12 is placed in an external actuation stage. The actuation stage forms the motor housing 33. Rather than handheld use, the actuation stage provides control for rotation and translation to be automated. The operator is then able to tele-operate the catheter from a remote console or a high-level motion planning algorithm may be used to generate spatial trajectories for the catheter tip 32.

The controller 27 is a processor, application specific integrated circuit, integrated circuit, digital signal processor, field programmable gate array, or other control device for controlling the motors 25. The controller 27 is configured by design, hardware, and/or software to steer the catheter 12. User input, imaging or sensing feedback, and/or pre-planning is used to control the motors 25 to bend the catheter 12.

In one embodiment, the controller 27 is configured to steer the catheter 12 in the patient frame of reference to maintain the position of the tip 32 by altering the bend(s) 51, 53 during the rotation. The controller 27 receives signals from the rotation sensor 23. The magnitude of rotation, rate of rotation, and/or absolute angle is translated to control signals for the motors 25 to change or alter the bend to maintain the position of the bend(s) 51, 53 and/or tip 32 relative to the patient during the rotation. The controller 27 actuates one or more motors 25 to change the amount of force applied to the steering wires 30, altering the steering to change the bend(s) 51, 53 to account for rotation or for other purpose. The bending plane relative to the catheter is kept in a same position for handle rotations using the orientation measurement of the catheter handle 21. The control allows for the orientation of the catheter 12 bending planes to be expressed with respect to a fixed world coordinate system. If the patient is registered within the world coordinate frame, or a registration is approximated according to the positioning of the patient, the bending of the catheter tip 32 may therefore be expressed with respect to the patient's anatomy. The rotation causes the ultrasound transducer array 14 and a corresponding field of view 18 to rotate while the position is maintained. This compensation allows the user to rotate the view plane or field of view 18 without affecting the position of the catheter tip 32. Active orientation by the controller 27 accounts for the rotation.

The controller 27 establishes the patient frame of reference based on an initial position of the handle with respect to rotation. The compensation compensates for any rotation from the initial angle. In a further embodiment, the patient frame of reference is based on a registration of the catheter frame of reference with a medical image. For example, an x-ray image (e.g., fluoroscope image) is taken of the patient with the catheter 12 within the patient. Data processing is applied to identify the location of the catheter with respect to the x-ray imager and the position of the patient with respect to the x-ray imager. The position of the catheter 12 with respect to the patient is determined by spatial transform of the coordinate systems. The patient is registered within the world coordinate frame or a registration is approximated according to the positioning of the patient. Once registered, the bending of the catheter may be expressed with respect to the patient's anatomy.

In one embodiment, the operating clinician steers the distal end of the catheter 12 using the integrated knobs as the user inputs 29 in a hand-held fashion. The motor controller 27 then decomposes the desired catheter bending as indicated by the operator into motor commands distributed over the three circularly-arranged tendons or steering wires 30. In this embodiment, translation and rotation of the catheter tip 32 are achieved by manually moving the active catheter handle. Steering may be done in the catheter frame of reference.

In other embodiments, the controller 27 is configured to control the motors 25 based on landmarks detected using scanning from the ultrasound transducer array 14. The acquired image is used in a feedback loop to control the catheter 12. For example, a landmark (e.g., anatomy such as a lesion or a device such as a catheter) is detected. The controller 27 operates the motors 25 to bend the catheter to place the array 14 to image the landmark from a different view point or to image anatomy positioned at an estimated location relative to the landmark. In one embodiment, the ultrasound image is used to generate control commands for the motors 25 according to a desired target pose in the image. The catheter 12 is therefore able to track landmarks in the patient geometry or track tools required for the intervention even during motion. The motors 25 are activated to maintain the landmark in the field of view of the array 14.

The array 14 connects to the beamformer 24. The beamformer 24 includes a plurality of channels for generating transmit waveforms and/or receiving signals. Relative delays and/or apodization focus the transmit waveforms or received signals for forming beams and setting a focal location. The beamformer 24 connects with the conductors 22 for applying waveforms for imaging with the array 14.

For imaging, the beamformer 24 selects an aperture including one, some, or all of the elements 16 of the array 14. Different apertures may be used at different times. The aperture is formed by using the elements 16 for transmit and/or receive operations using all or a sub-set of the elements 16. For scanning, the beamformer 24 electronically focuses along the azimuth direction. A plurality of scan lines using an aperture is scanned. During receive operations, the focus may vary as a function of depth (i.e., dynamic focusing). An elevation focus is provided by a lens and/or element sensitivity, or the array 14 is not focused in elevation. In alternative embodiments, the beamformer 24 connects with elevation spaced elements for at least partial electric focusing and/or steering in the elevation dimension.

The image processor 26 is a detector, filter, processor, application specific integrated circuit, field programmable gate array, digital signal processor, control processor, scan converter, three-dimensional image processor, graphics processing unit, analog circuit, digital circuit, or combinations thereof. The image processor 26 receives beamformed data and generates images on the display 28, which is a display screen. The images are associated with a two-dimensional scan. Alternatively or additionally, the images are three-dimensional representations. Data representing a volume is acquired by scanning. The image processor 26 renders an image from the data representing the volume.

Figure 6:
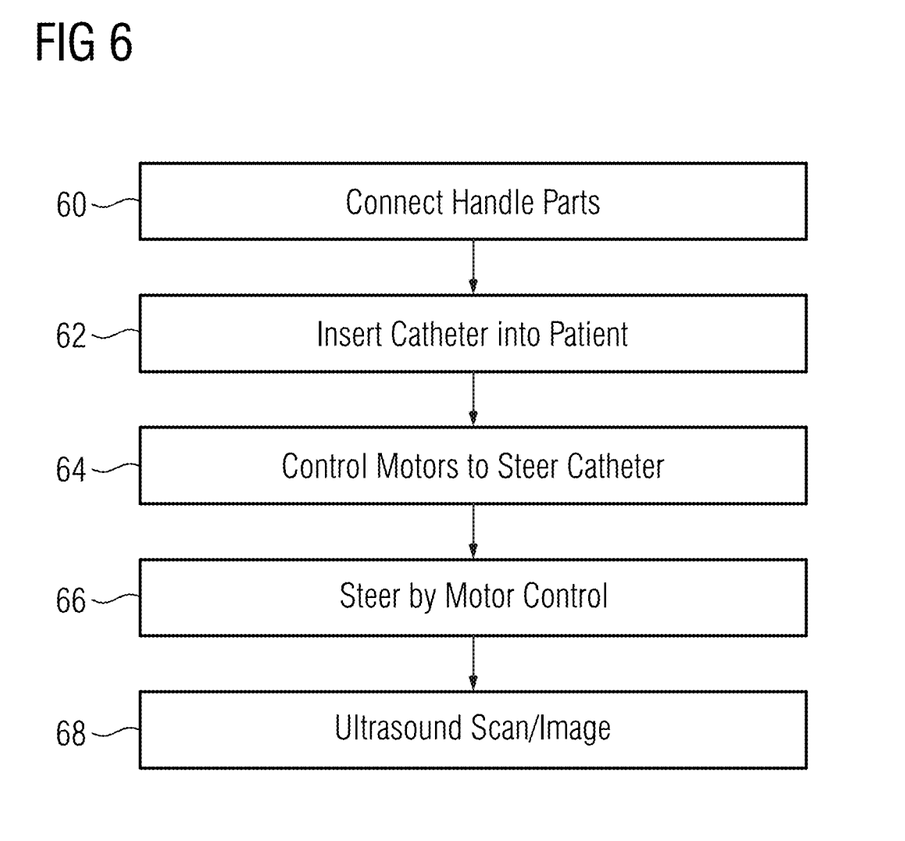
FIG. 6 is a flow chart diagram of one embodiment of a method for steering an ICE catheter.

FIG. 6 is a flow chart diagram of one embodiment of a method for controlled bending of an ICE catheter. The method includes a method for steering the catheter. The catheter is steered using motors integrated in the handle. The motors are subjected directly to the tension from the steering wires for steering without or with little slack.

The method is implemented by the system and/or ultrasound imaging catheter of FIGS. 1-5. Alternatively, a different catheter or system is used.

Additional, different, or fewer acts may be provided. For example, act 60 is not provided.

The acts are performed in the order shown or a different order. In the example of FIG. 6, acts 64 and 66 are performed as part of the catheter being steered, so are performed at a same time or in any sequence. For different embodiments, act 68 is performed after act 60, such as during acts 62, 64, and/or 66.

In act 60, a user connects handle parts together. The handle parts are snap fit, clipped, or pressure fit together. For example, a motor part is placed against a steering wire part. The two parts are twisted or rotated relative to each other to lock, snap, thread, or pressure fit together. The connection mates the shafts of motors with the steering wires or extensions from the steering wires. In alternative embodiments, the handle is not separated or separable.

The connection may include a choice. The user may choose the motor and/or steering wire parts to use together. Different combinations may be possible.

In act 62, the catheter is inserted into the patient. The catheter is translated along the longitudinal axis. The distal end and tip are inserted into the patient. Any length of catheter may be inserted. As the catheter progresses into the patient, the catheter may bend and/or twist with the vessel into which the catheter is inserted. The user may use steering to guide the catheter, such as applying force to steering wires to bend the catheter to progress in a given direction.

The handle, connected to the rest of the catheter, controls the translation and/or steering for insertion. The control uses manual movement of the handle and/or entry on input devices.

While the catheter is within the patient, the user may rotate the catheter. The catheter rotates about the longitudinal axis. For any bends caused by the vessel path, the catheter flexes to maintain the bend. For any bends caused by steering (i.e., force applied by the steering wires), the catheter resists flexing to bend with the vessel. Where the bend is in a chamber, the rotation of the catheter may not change the bend. The rotation of the catheter would cause the plane of the bend to rotate. Rather than steering with respect to the catheter and accepting the rotation of the plane of bending, the bend may be controlled to alter during rotation so that the plane of the bend is fixed or changes less than 10 degrees (e.g., maintained) relative to the patient. Motors alter the bend.

In act 52, the rotation of the catheter is optionally sensed. The rotation is sensed by a camera, inertial measurement unit, strain gauge, operation of an input to cause rotation, or another sensor. The rotation of the handle and/or other part of the catheter is sensed. The rotation of the catheter along the longitudinal axis of the catheter is sensed. The sensor may be on or in the handle, in another part of the catheter, or spaced from the catheter and handle. In alternative embodiments, rotation sensing is not provided.

In act 64, a controller controls one or more motors, such as linear motors, in a handle of the ICE catheter. For example, three, four, six, eight, or more motors are controlled. Different motors connect to different steering wires, so the relative forces by the different motors applied to the different steering wires controls active bending of the catheter. The motors for bending one, two, or more segments may be controlled.

In act 66, the ICE catheter is steered by the motor control through a steering wires connected with shafts of linear motors. One or more bends are formed by active control of force provided by the motors. Different segments may be bent differently or independently through control of different groups of motors.

The controller connected with one or more motors, which are connected to steering wires, steers the catheter. In one embodiment, the steering is with respect to the patient reference frame. Rather than steering with respect to the catheter reference frame of the catheter, the controller controls the motors to receive inputs from the user for steering with respect to a current position in the patient. Any bending or straightening by controlled steering is entered as a change relative to the patient. The controller translates the patient reference frame changes to the catheter reference frame for motor control. Where rotation is not occurring, the patient and catheter frames of reference may be aligned. Alternatively, the catheter frame of reference is registered with the patient frame of reference so that an input to bend relative to a patient direction (e.g., bend in a coronal plane of the patient or bend towards a valve of the heart) is transformed by the controller to a bend relative to the catheter so that the bend by the catheter in the catheter reference frame is performed to provide the desired bend in the patient frame of reference.

During rotation, the steering is performed to maintain any bending planes of the catheter in positions relative to the patient during rotation of the catheter about a longitudinal axis of the catheter. For imaging, the transducer (e.g., array) is maintained at a same location relative to the patient while the transducer and corresponding field of view are rotated. To maintain the position of the transducer, which is distal to the steering-caused bend, the bend in the catheter is changed. One or more motors, such as in the handle of the catheter, are operated to increase or decrease the forces (e.g., extend or draw in) in the steering wires relative to each other. As the rotation occurs, the bend is altered. The amount of bend (e.g., angle along the longitudinal axis), center of the bend, and/or length of the bend along the catheter is the same or maintained but the angle of the bend about the longitudinal axis changes. Alternatively, any characteristic of the bend may be altered to maintain the position of the tip or transducer, such as to account for interfering anatomy. The bend is altered in one or more ways so that a portion of the catheter distal to the bend remains at a location while also rotating the catheter about the longitudinal axis. The controller alters the bend in the catheter caused by steering so that the transducer of the catheter separated from a handle by the bend remains at a location relative to a patient.

The transducer may be rotated about the longitudinal axis, allowing shifting the field of view to image different directions due to the rotation. This rotation of the transducer occurs while the transducer is otherwise maintained in position, at least due to rotation about the longitudinal axis. Motion due to other sources, such as translation along the longitudinal axis, patient motion, and/or unintentional change from the user may cause shift in position while the controller maintains the position with respect to the bend.

The amount of alteration or the change in the steering is based on the sensed rotation. To maintain position, the alteration matches the rotation. The controller responds to the sensed rotation to perform a corresponding alteration in the bend in the catheter.

In other embodiments, the steering is with respect to the catheter frame of reference. By using motors, slack and resulting sluggish control may be avoided. User fatigue in applying the forces for steering may be avoided. Feedback or other control criteria in addition to or as an alternative to manual steering may be used to steer through the control by motor.

In act 68, the transducer is used for ultrasound scanning in a field of view. Ultrasound imaging is performed with the transducer. The user may view the surrounding tissue in different directions by rotating the catheter. Changes in bending may alter the field of view to image other anatomy or devices in the patient. Active bending may be used to keep anatomy or a device in the field of view of the transducer despite movement of the transducer and/or the patient.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A medical ultrasound system for intra-cardiac echocardiography, the system comprising:
   an intra-cardiac echocardiography catheter having a tip, a handle, steering wires, and an ultrasound transducer array; and
   a plurality of motors connected without gearing to the steering wires of the intra-cardiac echocardiography catheter, the motors being in the handle of the intra-cardiac echocardiography catheter; wherein ends of the steering wires connect with sliders configured to slide longitudinally in the handle, shafts of the motors connected with the sliders where the motors are configured to move the shafts longitudinally, which moves the sliders longitudinally, which applies push or pull force to the steering wires,
   wherein the handle comprises a steering wire housing part connected to the intra-cardiac echocardiography catheter and a motor housing part connected to a power cable and housing the motors, the steering wire housing part releasable from the motor housing part, wherein the motor housing part is configured to operate with different steering wire housing parts, the steering wire housing parts being disposable and the motor housing part being reusable.

2. The medical ultrasound system of claim 1 wherein the ultrasound transducer array comprises a one-dimensional array of transducer elements for scanning a patient within the field of view, the one-dimensional array being on a distal end of the intra-cardiac echocardiography catheter for insertion within the patient.

3. The medical ultrasound system of claim 1 wherein the steering wires control a bend at a distal end of the intra-cardiac echocardiography catheter.

4. The medical ultrasound system of claim 1 wherein two groups of at least three steering wires per group connect to different segments at different positions along an insertable portion of the intra-cardiac echocardiography catheter, the insertable portion insertable within a patient.

5. The medical ultrasound system of claim 4 wherein the steering wires of one of the two groups connect to a first rigid plate in one of the different segments, and the steering wires of another of the two groups connect to a second rigid plate in another of the different segments.

6. The medical ultrasound system of claim 1 wherein the motors comprise linear motors.

7. The medical ultrasound system of claim 1 wherein shafts of the motors directly connect to the steering wires.

8. The medical ultrasound system of claim 1 wherein shafts of the motors have shaped ends releasably mateable with holders connected to the sliders, the steering wire housing part connectable with the motor housing part by rotation to mate the shaped ends with the holders.

9. The medical ultrasound system of claim 1 further comprising a rotation sensor in the handle, and a controller configured to maintain a position of the tip relative to a patient during rotation of the handle by actuation of one or more of the motors in response to sensed rotation from the rotation sensor.

10. The medical ultrasound system of claim 1 further comprising a controller configured to control the motors based on landmarks detected using scanning from the ultrasound transducer array.

11. The medical ultrasound system of claim 1 further comprising one or more input sensors on the handle, the input sensors configured for steering the intra-cardiac echocardiography catheter from user input based on control of the motors.

12. The medical ultrasound system of claim 1 wherein the motors are arranged within the handle concentrically around a central region.

13. A medical ultrasound system for intra-cardiac echocardiography, the system comprising:
- an intra-cardiac echocardiography catheter having a tip, a handle, steering wires, and an ultrasound transducer array; and
- a plurality of linear motors connected to the steering wires of the intra-cardiac echocardiography catheter, the motors being in the handle of the intra-cardiac echocardiography catheter;
- wherein ends of the steering wires connect with sliders configured to slide longitudinally in the handle, shafts of the linear motors connected with the sliders where the linear motors are configured to move the shafts longitudinally, which moves the sliders longitudinally, which applies push or pull force to the steering wires,
- wherein the handle comprises a steering wire housing part connected to the intra-cardiac echocardiography catheter and a motor housing part connected to a power cable and housing the linear motors, the steering wire housing part releasable from the motor housing part,
- wherein the motor housing part is configured to operate with different steering wire housing parts, the steering wire housing parts being disposable and the motor housing part being reusable.

14. The medical ultrasound system of claim 13 wherein the linear motors and steering wires comprise two or more groups connected to steer two or more segments of the intra-cardiac echocardiography catheter.

15. The medical ultrasound system of claim 13 wherein the handle has a first part releasably connectable to a second part, the first part housing the linear motors and the second part having a termination end of the steering wires at the sliders.

\* \* \* \* \*